United States Patent [19]

Franks

[11] 4,340,815
[45] Jul. 20, 1982

[54] PREPARATION OF MATERIAL FOR EXAMINATION BY TRANSMISSION ELECTRON MICROSCOPY TECHNIQUES

[75] Inventor: Joseph Franks, Teddington, England

[73] Assignee: Ion Tech Limited, Teddington, England

[21] Appl. No.: 150,745

[22] Filed: May 19, 1980

Related U.S. Application Data

[63] Continuation-in-part of Ser. No. 957,849, Nov. 6, 1978, abandoned.

[30] Foreign Application Priority Data

Nov. 7, 1977 [GB] United Kingdom ............... 46311/77

[51] Int. Cl.³ .......................................... G01N 23/00
[52] U.S. Cl. .................................. 250/307; 250/311
[58] Field of Search ............. 250/442, 397, 398, 309, 250/492 A, 492 B; 219/121 EJ, 121 EK

[56] References Cited

U.S. PATENT DOCUMENTS

| | | | |
|---|---|---|---|
| 3,206,598 | 9/1965 | Wegmann | 250/309 |
| 3,548,189 | 12/1970 | Meinel et al. | 250/492 B |
| 3,699,334 | 10/1972 | Cohen et al. | 250/492 B |
| 3,944,873 | 3/1976 | Franks et al. | 313/206 |
| 4,128,765 | 12/1978 | Franks | 250/398 |

*Primary Examiner*—Bruce C. Anderson
*Attorney, Agent, or Firm*—Irvin A. Lavine

[57] ABSTRACT

Method and apparatus for preparing a specimen for observation under the electron microscope by ion erosion. A saddle-field ion source is employed to irradiate the specimen with the specimen held in close proximity spacing with respect to the cathode aperture of the ion source. Such close proximity spacing ensures that the specimen is thinned at a rapid rate comparable with the rates attained with chemical etching.

17 Claims, 7 Drawing Figures

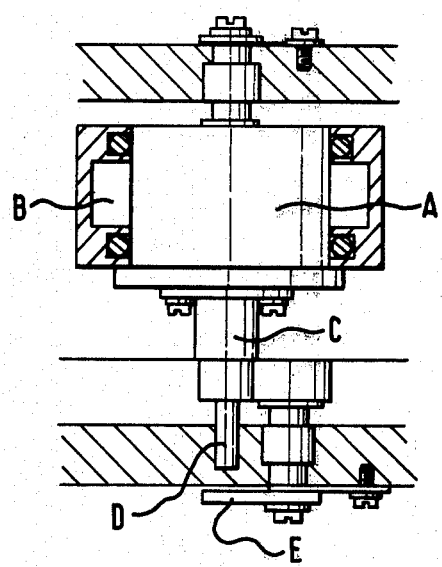
FIG.1.
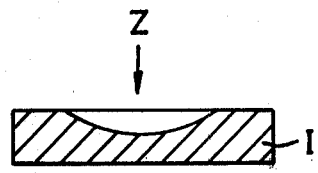
FIG. 2a.
FIG. 2b.
FIG. 2c.
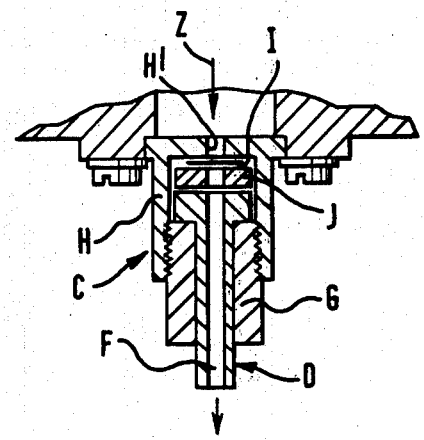
FIG. 3.
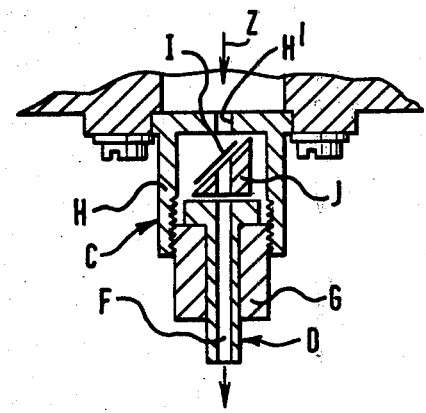
FIG. 4.

PREPARATION OF MATERIAL FOR EXAMINATION BY TRANSMISSION ELECTRON MICROSCOPY TECHNIQUES

CROSS REFERENCE TO RELATED APPLICATION

This application is a continuation-in-part of my application Ser. No. 957,849 filed Nov. 6th 1978 now abandoned.

FIELD OF THE INVENTION

The present invention relates to ion erosion thinning techniques for the preparation of materials for examination under the electron microscope.

BACKGROUND ART

The high resolution attainable with transmission electron microscopy makes this an outstanding technique for examining the microstructure of materials. The direct examination of materials by transmission electron microscopy requires that the specimen to be examined is transparent to electrons. Consequently the thickness of the specimens must be restricted to 100 to 200 nm.

It has therefore been necessary to develop methods for preparing thin specimens of materials that have widely varying mechanical and chemical properties. Soft materials such as biological specimens, may be prepared by microtoming, although difficulty is sometimes encountered when hard particles are present.

For some metals, semiconductors, and other inorganic materials, chemical etching and electrolytic techniques are suitable. In one widely used method the material to be thinned is placed in a jet etching tank and the etching process observed through a lens with a light source behind the specimen.

The etching action of the jet is continued until perforation of the specimen occurs. Since the etching action is stronger at the centre of the jet than at its periphery, perforation starts at the centre and spreads towards the periphery. Thus the etching process is immediately arrested when perforation occurs by flushing the specimen with an inhibiting wash, leaving adjacent areas around the perforation which are usually sufficiently thin to allow micrographs to be taken during examination under the electron microscope.

Difficulties arise with such chemical etching methods when materials are not homogeneous. Thus preferential etching may occur, second phases may be leached out, and in semiconductors p-type material may etch at a different rate from n-type material. Even when a material can be controllably etched, the etchant may form a contaminating layer on the surface.

For materials for which suitable chemical etchants do not exist, such as some glasses, ceramics, and geological specimens, various mechanical preparation techniques have been tried. The specimen may be crushed and fine slivers selected, or thin sections may be produced by very careful mechanical polishing. These operations require considerable skill and can generally not be applied to brittle granular materials with voids.

However a large variety of materials which do not lend themselves to chemical treatment, are thinned by ion erosion. Ion erosion has proved an increasingly valuable tool to electron microscopists especially those engaged in examining classes of material such as ceramics, impurity-doped semiconductors and alloys. These materials are difficult to etch chemically or can contain constituents that etch at widely differing rates. Where chemical or electrolytic etching are possible however the liquid techniques are still favoured because the equipment is generally less costly, the etching rate is faster and of course there is no radiation damage although specimens may suffer chemical contamination.

Because of the relatively slow ion etching rates materials are commonly prethinned by mechanical or chemical means or a combination thereof. Some specimens may be prethinned to say 25 $\mu$m quite readily, in other cases a considerable amount of skill and patience may be required. In other cases specimens cannot be prethinned to less than a few hundred micrometers because the material may be friable and crumble or inclusions may be lost from the matrix.

In typical known ion thinning equipment ion beams of about 2 mm diameter from two sources impinge centrally on either side of a specimen. A hole or perforation is allowed to form in the specimen by the ion beam, which acts in a similar way to the chemical jet during chemical etching, when the ion beam is immediately turned off to leave adjacent thin areas around the perforation transparent to electrons. The ion current from each source may be about 100 $\mu$A, and the cathodes of the source from which beams emerge are at a distance of about 4 centimeters from the specimen. Under these conditions the thinning rate to penetration for most specimens is in the range of 1 to 10 $\mu$m/hr and for many specimens the rate is near 3 $\mu$m/hr.

A typical sample thickness is 50 $\mu$m. Assuming therefore an ion thinning rate of 3 $\mu$m/hr it would take 16 hours to thin the specimen to penetration by ion erosion.

Some materials 125 micrometers thick, may take two to three days to thin by ion erosion, although in one case an etch rate of 15 $\mu$m/hr has been claimed. Even for this relatively fast rate, chemical etching is one or two orders of magnitude faster.

The etch rate of course depends on the material, and a generally accepted rate for ceramics is 1 to 2 $\mu$m/hr with a glancing angle of 20° and an ion current density of 200 $\mu$A/cm$^2$. Where possible therefore samples are prethinned to 20 to 30 $\mu$m although porous or friable materials are generally thicker.

SUMMARY OF THE INVENTION

It is an object of the present invention to extend the use of ion erosion as a technique for thinning specimens for observation under the electron microscope by increasing the etching rate to equal or approach that of chemical etching.

The saddle-field ion source is suitable for use in ion erosion techniques. An example of such a source is the subject of U.K. Pat. No. 1,488,657 or U.K. Pat. No. 1,158,782 and corresponding U.S. Pat. No. 3,484,602.

It has been normal practice to hold specimens to be eroded in the beam path of such a source at several cms. from the cathode aperture where the current density is but a few $\mu$A/mm$^2$. It has been found however that much higher current densities exist at the centre of the beam of the saddle-field ion source within a very small distance from its cathode aperture.

Thus the current density up to a distance of 2 cms from the cathode aperture is in excess of 35 $\mu$A/mm$^2$ at 5 kV with a diameter of 0.12 mm. At increased distances the beam spreads so that a distance of 6.5 cms, about the distance at which specimens are normally held, the current density of the beam at its centre has decayed to 3.5 μA/mm².

The existence of such a rapid decay in current density has hitherto not been appreciated. Since the etching rate of the beam is in direct proportion to its current density, clearly close proximity spacing of the specimen to be eroded to the cathode aperture than has previously been the case, will result in faster erosion of the specimen to penetration.

The high concentration near the cathode aperture is maintained because it has been found that a large proportion of the beam in that area consists of excited energetic neutrals. Thus the ion/neutral ratio over a distance of 6.5 cms from the cathode aperture assumes a bell-shaped distribution. At a distance of 1 cm the ion/neutral ratio is 1.5 at the centre of the beam while at approximately 2 cms the ratio has increased to 5 and evidently a large proportion of the excited neutrals have become ionized.

At a distance of 6.5 cms the ion/neutral ratio is again 1.5, most of the ions have been repelled from the centre of the beam and flux density, and hence the etching rate, is therefore much reduced.

The phenomena involved is still a matter of study but it is postulated that the ions produced within the source combine with secondary electrons produced at the cathode aperture forming excited neutrals, a considerable proportion of which subsequently dissociate into ions and electrons.

Accordingly the object of the invention is achieved in the provision of a method, and apparatus for carrying out the method, characterised in that a specimen to be thinned is placed in close proximity spacing with respect to the cathode aperture of a saddle-field ion source and the beam of the source is concentrated on one spot on the specimen within the close proximity spacing to rapidly thin the specimen to penetration without deleteriously affecting its structure.

The distance of the specimen from the cathode aperture may be varied from almost touching to about 2 cms.

The specimen may be held stationary close to the ion source at normal incidence or at any convenient angle, for example 60° from the normal. Alternatively the specimen may be mounted on a rotating stage.

Since the beam is concentrated on one spot on the specimen, the specimen may be cooled to avoid overheating in the case of heat sensitive materials. This is achieved by cooling the specimen holder with running cold water and regulating the intensity of the beam. Since the specimen holder is close to the ion source, the ion source is cooled as well.

It is not desirable to allow the temperature of the source to rise above 300° C. to maintain efficiency. Thus for example the source may be additionally cooled by being encased in a water cooled jacket.

Cooling of the source allows more power to be applied and hence higher output. It has also been found that as the output is increased, which involves a slight increase in gas pressure, the neutrals content of the beam increases within the close proximity spacing of the specimen and source.

The cooling system maintains the ion source below 300° C. when operating at maximum power (8 kV, 5 mA) giving a flux of particles equivalent to about 500 μA of 7 kV ions, and the specimen temperature will stabilise at less than 120° C.

For heat sensitive materials the specimen temperature may be further reduced by decreasing the beam current. Thus woods metal with a melting point of 60° C. has been successfully thinned without melting by reducing the beam current to 30 μA equivalent. The thinning rate in this case was still very fast (100 μm/min) because of the sputtering properties of the material.

If the erosion rate and thickness of the specimen are known the process may be stopped after a set time when a sufficiently thin area has been produced for a final short treatment in conventional ion thinning equipment.

The fast thinning process according to the invention may conveniently be terminated automatically by placing a detector behind the specimen. When the specimen is penetrated an ion current is detected and when this current reaches a predetermined value, for example 50 nano amperes, the ion source is switched off.

In accordance with one preferred mode of operation, the specimen is eroded for a short time from one side to remove any mechanical damage or chemical contamination, then reversed and thinned to penetration. The specimen may then be finally thinned in conventional equipment, preferably with the ion beam impinging on the specimen at near glancing incidence. The final erosion process will mainly occur on the shallow etched side, as the thinned region on the reverse side will largely be shielded by the unetched periphery of the specimen.

The etching rate achieved with the specimen mounted in close proximity spacing to the ion source cathode is about a factor of 40 faster than the rate with conventional ion thinning methods. For example utilising the present technique a specimen of silicon nitride 240 microns thick has been thinned to penetration in 70 minutes.

BRIEF DESCRIPTION OF THE DRAWINGS

Other features which may be included in accordance with the invention will be more readily appreciated from the embodiments thereof shown, by way of example, in the accompanying drawings in which:

FIG. 1 is a general view of an ion thinning arrangement according to the present invention with a stationary specimen;

FIGS. 2A, 2B and 2C illustrate various stages in the erosion of a specimen by an ion beam;

FIG. 3 is a detailed view showing a specimen mounted normally to the ion beam;

FIG. 4 is a detail showing the specimen mounted at an angle to the ion beam.

DETAILED DESCRIPTION OF PREFERRED EMBODIMENTS OF THE INVENTION

Figure 5:
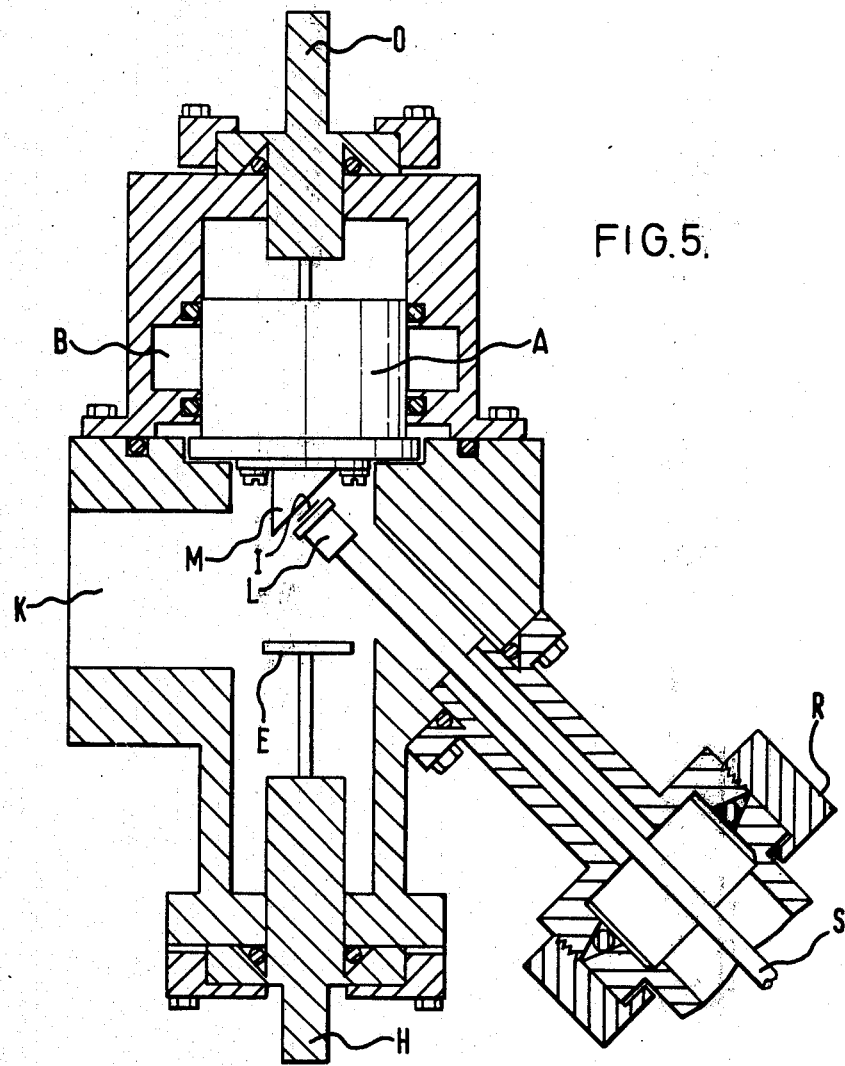
FIG. 5 shows the specimen mounted on a rotating stage.

The ion thinning apparatus shown in FIG. 1 comprises an ion source A of the saddle-field type surrounded by a water cooling jacket B.

The saddle-field ion source is provided with a cathode C from which emerges a beam of ions when the ion source is energised.

A specimen carrier D bearing a specimen (not shown), is placed in the path of the beam emerging from the cathode aperture of the cathode C so that over a period of time the beam penetrates the specimen.

The specimen is held in close proximity spacing with respect to the cathode aperture and preferably within a critical range of 2 cms therefrom where the intensity of the ion beam at its centre is the greatest, so that rapid thinning of the specimen is achieved.

A detector plate E is mounted behind the specimen carrier D and when the specimen has been penetrated by the ion beam the detector plate E senses such penetration by measuring the ion current received. When the current received by the plate E reaches a set value the source is automatically switched off. The arrangement is such that the source is arranged to be switched off just after penetration of the specimen so that thin areas remain around the penetration, perforation or hole in the specimen, transparent to electrons.

The various stages in the erosion of the specimens by the ion beam is illustrated in FIGS. 2A, 2B and 2C.

The strength of the ion beam is more intense at its centre than at its periphery, and hence the etching action decreases from the centre towards the periphery of the beam.

Thus the erosion profile in the specimen as shown, assumes a dished appearance which works its way through the specimen with time as shown in FIGS. 2A, 2B and 2C until perforation occurs and a pheripheral area is left around the perforation thin enough to allow passage of electrons. Thus micrographs of the structure of the specimen may be obtained upon examination under the electron microscope.

FIG. 3 shows the cathode C of the arrangement of FIG. 1 in cross-sectional detail and wherein a specimen I is shown positioned normal to the direction of the ion beam Z.

The specimen carrier D is held within a cathode housing H by means of a carrier insert G. The cathode housing has a cathode aperture G' from which emerges the ion beam Z. The insert G is screw mounted for adjustment in the housing H so that the specimen can be positioned at the required critical distance from the aperture H'. The carrier D has a passage F positioned to be in alignment with the beam Z so that the plate E is able to detect the presence of an ion current when penetration of the specimen I has occurred.

A flat spacer plate is provided for mounting the specimen I normal to the ion beam Z and in front of the cathode aperture H' of the cathode C.

The arrangement of FIG. 4 is identical to that of FIG. 3 with the exception that the spacer plate J is prismatic or suitably angled to allow the specimen I to be positioned at an angle to the direction of the ion beam Z, which angle may be about 60° from normal for an optimum thinning rate.

As with the FIG. 3 arrangement the distance of the specimen I from the cathode aperture H' can be varied by means of the screw mounted clamping insert G and within the critical range of the aperture.

In the arrangement shown in FIGS. 1, 3 and 4 the source A is cooled by provision of water jacket B as mentioned, and additionally the specimen carrier D may be water cooled by, for example, circulating water. Since the specimen is mounted in close proximity spacing to the cathode aperture H', cooling of the specimen holder D will in effect provide a cooling effect to the source, and cooling of the source by water cooling jacket B will also cool the specimen.

In the system shown in FIG. 5 the specimen is positioned on a specimen carrier L mounted to a rotatable shaft S.

The rotating stage, comprising the carrier L and shaft S, is mounted in a self contained vacuum-tight unit which may be attached to the port of a pumping system.

The unit comprises a pumping port K, and is mountable to the base of the ion source A of the type described in FIGS. 1, 3 and 4.

The source A of FIG. 5 however has an angled cathode configuration M so that the specimen I can be mounted on the carrier L and positioned such that the beam from the source A is at an angle to the normal of the specimen.

The unit is provided with a quick release vacuum coupling R and the shaft S may be connected to a rotary drive motor through a vacuum seal (not shown). With this arrangement upon unscrewing of the vacuum coupling P the specimen carrier L may be withdrawn from the vacuum chamber and a specimen conveniently loaded.

The apparatus as described can be used to thin specimens to penetration at rates approaching or equalling those attained by chemical methods.

This is achieved, as mentioned earlier, by making use of the newly discovered feature that the intensity at the centre of the ion beam of the saddle-field source is the greatest within a critical range of 2 cms from its cathode aperture.

The content of the ion beam close to the cathode aperture has been found to consist of three species of particles namely ions, excited energetic neutrals and neutrals, the excited energetic neutrals being ions having loosely bound electrons.

These excited neutrals are believed to be formed by secondary electrons, which are produced at the cathode aperture, combining with ions produced within the source.

The ion/neutral ratio at the centre of the ion beam has been found to increase with distance from the cathode aperture to a maximum at 2 cms therefrom, and to fall again as the distance increases.

Thus assuming that the total number of particles in the beam remains constant it is clear that the number of excited energetic neutrals must decrease with increasing distance from the cathode aperture. The excited neutrals are therefore losing their electronic charge as they move away from the aperture to revert to ions and have decayed substantially in number at the 2 cm distance from the cathode aperture.

The ion/neutral ratio at the centre of the beam begins to fall beyond the 2 cm range due to the absence of the energetic neutrals and the fact that most of the ions have been repelled from the beam centre causing the beam to spread with consequent reduction in beam intensity and reduced erosion capability.

Clearly the 2 cm range is critical to the achievement of rapid thinning because it is within this range that the greatest number of ions and energetic neutrals exist at the centre of the beam which produce the eroding process.

In previously known techniques only ions in the beam have contributed to the eroding process. The present method uses a combination of ions and energetic neutral particles to produce erosion which consequently takes place at a faster rate due to the much greater intensity of the ion beam.

What I claim is:

1. A method of preparing specimens suitable for examination by electron microscopy techniques comprising providing a saddle-field ion source for producing a beam of ions, placing the specimen in front of a cathode aperture of the ion source, and irradiating one spot on the specimen by the beam to erode its surface, the specimen being held within a range from almost touching the cathode aperture to substantially 2 cms therefrom during irradiation to thereby rapidly erode the specimen to penetration and produce an area surrounding the penetration of suitable thickness for transmission of electrons.

2. A method as claimed in claim 1 wherein the specimen is held at said spacing from the cathode at normal incidence to the beam.

3. A method as claimed in claim 1 wherein the specimen is held at an incidence angle to the beam.

4. A method as claimed in claim 3 wherein said angle is 60° C.

5. A method as claimed in claim 4 wherein the specimen is rotated during irradiation.

6. A method as claimed in claim 5 further including an initial step of eroding the specimen for a short time on one side to remove mechanical damage or chemical contamination, and then reversing the specimen to irradiate the other side to said required thickness.

7. A method as claimed in claim 1 wherein the ion source is cooled.

8. A method as claimed in claim 1 wherein the specimen is cooled.

9. Apparatus for preparing specimens suitable for examination by electron microscopy techniques comprising a saddle-field ion source provided with a cathode aperture, for producing a beam of ions, holding means for adjustably supporting a specimen from almost touching to substantially 2 cms from the cathode aperture for irradiation of one spot thereof by the beam to thereby rapidly erode the specimen to penetrate and provide an area surrounding the penetration of suitable thickness for transmission of electrons.

10. Apparatus as claimed in claim 9 wherein the specimen holder is adapted to hold the specimen at normal incidence to the beam.

11. Apparatus as claimed in claim 9 wherein the specimen holder is adapted to hold the specimen at an incidence angle to the beam.

12. Apparatus as claimed in claim 11 wherein the specimen holder is rotatably mounted to permit rotation of the specimen in the beam.

13. Apparatus as claimed in claim 12 including detector means placed downstream of the specimen in a position to be irradiated by the beam after penetration thereby of the specimen, and operably responsive to ion current to automatically turn off said source after the ion current has reached a predetermined value.

14. A method as claimed in claim 1 further including the step of detecting when penetration of the specimen has occurred and terminating irradiation of the specimen immediately as a result thereof.

15. Apparatus as claimed in claim 9 wherein said source comprises means for adjusting the concentration of the ion beam to a higher or lower level of concentration.

16. Apparatus for preparing specimens suitable for examination by electron microscopy techniques comprising a saddle-field ion source provided with a cathode aperture for producing a beam of ions having a proportion of excited energetic neutrals close to said cathode aperture, and holding means for supporting a specimen in that portion of the beam path containing said excited neutrals thereby to erode the specimen to penetration, wherein said portion of the beam containing said excited energetic neutrals is within a range of 2 cms from said aperture and said holding means is adjustable to support the specimen within said range.

17. A method for preparing specimens suitable for examination by electron microscopy techniques comprising providing a saddle-field ion source having a cathode aperture, producing a beam of ions from the source to emerge from the aperture containing a proportion of excited energetic neutrals close to said aperture, and holding the specimen in front of the aperture and in that portion of the beam path containing said excited energetic neutrals thereby to erode the specimen to penetration, wherein that portion of the beam containing said excited energetic neutrals extends from the cathode aperture to substantially 2 cms therefrom, the specimen being held within this range from said aperture.

* * * * *